July 1, 1952
J. D. BROWNELL
Plant Pat. 1,111
ROSE PLANT
Filed April 16, 1951
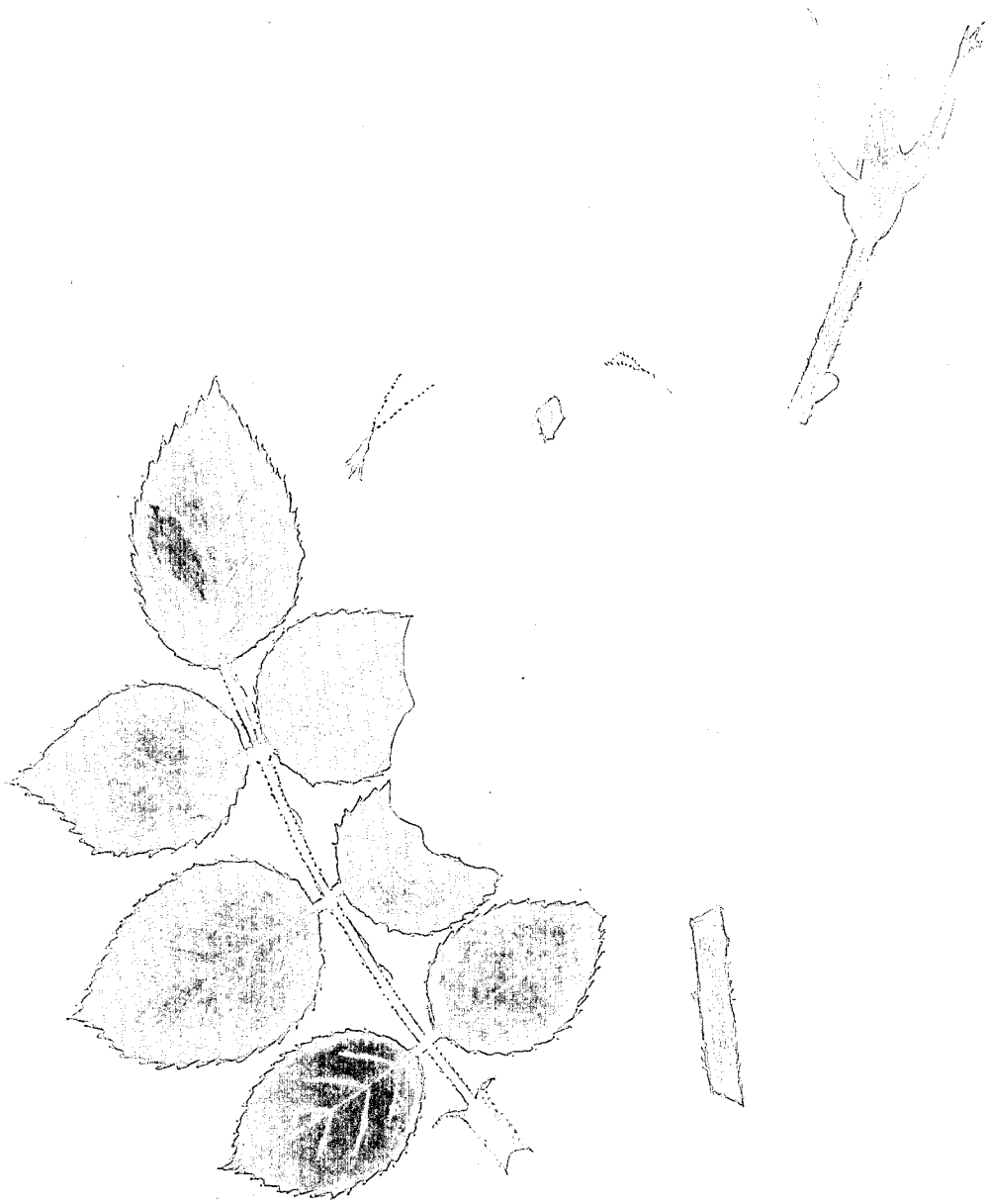
INVENTOR.
Josephine D. Brownell.

Patented July 1, 1952 Plant Pat. 1,111

UNITED STATES PATENT OFFICE 1,111

ROSE PLANT

Josephine D. Brownell, Little Compton, R. I.

Application April 16, 1951, Serial No. 221,251

1 Claim. (Cl. 47—61)

My invention relates to rose plants and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States:

The yellow shades (ordinary dictionary definition) of its petals, in combinations with the unique brilliance thereof and their tendency to hold this color under exposure;

The novelty and variation within certain definite limits of the form of the bloom, its character of holding that form for a long time, and the petallage of the flowers;

Its character of fragrance:

Its unusual abundance of flowers, notable after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by blackspot, under certain definite conditions of exposure, without any cultural control.

In the accompanying drawing forming a part of this specification I have shown my new rose in its natural colors, that is, as near as is possible to do so artificially.

My new rose is otherwise described as follows:

Type: Hybrid tea, *Rosa wichuraiana* hybrid, bush for garden display, cut flower and forcing or growing under glass.

Class: Hybrid tea crossed with *Rosa Wichuraiana*, further restricted by originator to include only those varieties that can survive moderately low sub-zero temperatures.

Breeding: This variety was produced and bred by me and under my direction by propagation and cross pollenation.

It came into being as a seedling grown from a seed borne on "Pink Princess" (Plant Patent 842), crossed as seed parent with "Free Gold" (unpatented).

The pollenation that fertilized the seed that grew into my new rose was directed by me and was performed by emasculating flowers and placing thereon a bag protecting from self and foreign pollen. These bags were later removed and the flowers were hand pollenated with a camel's hair brush and the bags immediately replaced. The date of this pollenation was July 6, 1946.[1] The seed was planted under my direction on December 18, 1946, and the date of the first flower was July 14, 1947.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1947–9 inclusive and the characters have successively reproduced, true to the original seedling.

*Flower*

Habit: It blooms out of doors in Little Compton, beginning about three days prior to the average beginning time of commercial hybrid teas and continues relative to growth of the plant until frost.

Flowers borne: Often one and frequently two or three or more on each stem, in the usual hybrid tea type of cluster. The pedicels and peduncles are medium small in diameter and medium in length, erect, stiff, almost smooth, free from large prickles and bristles but with a few very small prickles varying to small hairs. Stems are long, diameter medium to large and notably stiff and rigid.

Quantity of bloom: Free, being cumulative in quantity from year to year as the plant increases in size, flowering through the summer.

Fragrance: Distinctive, pleasing China tea in combination with that of *Rosa wichuraiana*, under favorable environment.

Bud: Neck normal as described, opens well, being little to not at all affected by hot or wet weather or both, as to color and form, except at very high temperatures the color is less intense and the form of the petals is less recurled.

Before the calyx breaks the size is medium, form moderately pointed, frequently with one or more sepals having foliaceous parts extending beyond the apex of the calyx up to about three quarters of an inch, the number and size of the foliaceous parts being variable and rarely having one or more narrow, pointed minutely serrate appendages on each side of the sepals, otherwise the sepals are usually normal and regular, tapering to lanceolate at their apex, turning back nearly perpendicular to the pedicel as the bud opens.

[1] This and other dates herein are approximate.

Color of the bud as the calyx opens: outside of the petals Sulfur Yellow at 1,[1] frequently splashed with a limited marking of Signal Red at 719/3. Inside same, except not splashed.

Bloom: As the bud opens and the flower develops to maturity the color both sides of petals slowly changes to 1/1, 1/2 and later to 1/3.

The flower usually varies in size around four to five inches in diameter, petals vary from twenty-five to fifty, frequently with some smaller petals and petaloids in the center, variable in number.

The flower opens high centered, often informal when larger number of petals, recurled, with display of stamens early with few petals, later with many. The petals are variable from ovate to obovate to irregular and frequently with surfaces variously warped and edges of the larger petals variously scalloped, and of the smaller petals and petaloids often notably irregular. Texture is medium to thick; both sides brilliant with slight veining. The time of opening in favorable conditions is four to five days.

The petals are substantial and after about six to seven days drop off cleanly, except that occasionally one or two inner petals of petaloids cling to turn dull, to fall later. The flower does not "ball" in wet weather. The flower lasts well, is not affected at any stage by moderate cold or hot temperatures, or by humidity or wet weather.

Reproductive organs:

*Stamens*, quantity variable, being of medium average length and slightly uneven in length.

*Anthers*. Apricot 609/2. Filaments, Carrot Red 612/3. The last two mentioned colors are slightly variable.

*Pistils* are several of slightly uneven lengths, averaging around one-half inch long.

*Ovaries* are usually all inclosed.

*Hips* frequently develop to ovoid to globular, color comparable with under side of leaves with variable colored overlay on the side exposed to the sun, moderately smooth; walls, thin, fleshy, medium in size.

*Sepals* are persistent and break off easily.

*Plant*

Foliage: Is abundant, of compound leaves of three to five leaflets near the flower, five leaflets lower down the stem and frequently seven leaflets in the middle of the stem and nearer the base. Size of leaflets medium, averaging in size a little larger than half way between the average hybrid tea and the *Rosa wichuraiana* leaflets. As the plants develop in size some of the leaflets develop to twice the size described above. The leaflets are abnormally thick and hard. They emit an unusual reflection of deep green (ordinary dictionary definition) texture. Form of leaflets usually ovate with apex moderately acute, base rounded frequently slightly acute, in some instances with the circumference on one side of the petiolule out of alignment with the other side by about one-sixteenth of an inch or less, margins with pointed serrations, petiolules short.

The leaflets average in width about two-thirds of their length.

Color of leaflets on the upper surface is approximately Sage Green 000861, with reverse side nearly Cyprus Green 59/3 frequently overlaid with trace of Geranium Lake 20.

[1] Color references unless otherwise noted are to British Horticultural Color Chart.

The rachises are medium, moderately narrow to slender, upper side smooth except some very short hairs on edges. Under side moderately smooth, usually 3 to 5 short prickles.

Stipules are medium to long, averaging about three-quarters of an inch long, with sharp points, the upper edges of which normally form an angle of about 100 degrees.

Habit, due to constitutional factors, becoming bushy to tall, upright, compact, more cumulative in growth from year to year than the normal hybrid tea rose plant, by stems from the base and by rebranching and growth and enlargement and extension of the stems from the base. The growth is moderately free at first, developing more rapidly after one or two years under favorable vegetative opportunity.

Color of mature stems is the same as that of the upper surface of mature leaves, shading variously lighter and also with slight overlay of Geranium Lake 20 variable in intensity.

Prickles, several, frequently two to four between leaves, averaging in length about one-quarter inch, shading from approximately Geranium Lake 20 to lighter at the base, turning lighter throughout and later to nearly colorless. Hairs few on upper portion of stems. Color of some prickles shading to color of stems.

Winter resistance: A notable characteristic of this new rose is the resistance to moderate sub-zero temperature in combination with its hybrid tea character and its *Rosa wichuraiana* ancestry. This variety with grafted bud and plant above that bud entirely exposed above ground to moderate sub-zero temperatures survived and bloomed normally the following season. The word "temperature" herein refers to the Fahrenheit scale.

Comparisons: V for Victory (Plant Patent 543) is of more spreading growth, the foliage lacks the reflection of deep green texture, are softer, many of the stems are very much smaller in diameter, so much so that they often weep somewhat, whereas the stems of my new rose are much greater in diameter, much more rigid and grow much more upright. The form of the flower differs in that the petals of the full open blooms of V for Victory are more formally concentrically arranged while those of my new rose are often irregularly arranged throughout.

Stargold (Plant Patent 248) blooms are completely formal in arrangement of petals, and this variety does not bloom as much through mid-season as does my new rose.

The leaflets of my new rose have shown no blackspot for three seasons from rose time until injured by frost or other injury. The other two varieties mentioned are somewhat susceptible to blackspot.

King Boreas (unpatented) is also somewhat susceptible to blackspot, the blooms are much smaller and bloom more after the manner of the polyanthas and of that class commercially known as "Floribundas."

I claim:

The new and distinct variety of rose plant as described and illustrated, characterized by its color, bloom cluster, resistance to disease and to moderate sub-zero temperatures, and by the characteristic color reflection of its leaflets.

JOSEPHINE D. BROWNELL.

No references cited.